United States Patent [19]
Ezzell et al.

[11] 3,937,710
[45] Feb. 10, 1976

[54] HYPOCHOLESTEROLEMIC COMPOUNDS

[75] Inventors: Bobby R. Ezzell, Houston, Tex.; Eugene R. Fluck, Berwyn, Pa.; Louis R. Haefele, Winston-Salem, N.C.

[73] Assignee: R. J. Reynolds Tobacco Company, Winston-Salem, N.C.

[22] Filed: Aug. 15, 1973

[21] Appl. No.: 388,366

Related U.S. Application Data

[60] Division of Ser. No. 198,445, Nov. 12, 1971, Pat. No. 3,781,444, which is a continuation-in-part of Ser. No. 105,076, Jan. 8, 1971, abandoned.

[52] U.S. Cl............. 260/297 R; 424/263; 424/323; 424/325; 424/327; 424/331; 260/296 M; 260/464; 260/563 R; 260/566 A; 260/586 M
[51] Int. Cl.²................. G07C 49/34; C07D 213/50
[58] Field of Search....... 260/566 A, 563 R, 586 M, 260/464, 296 M, 296 R, 297 R

[56] References Cited
OTHER PUBLICATIONS

Houghton et al., J. Chem. Soc. (C) 1969, pp. 978–981.
Cheronis et al., Semimicro Qualitative Organic Analysis, pp. 242–245, Thomas Y. Crowell Co. NY (1947).
Conia et al., Chemical Abstracts Vol. 67, Abst. No. 21473e (1967).
Braude et al., J. Chem. Soc. 1957, pp. 4711–4719 (1957).
Cornubert et al., Bull. Soc. Chim. 5 (1938), pp. 1490–1501.

*Primary Examiner*—John D. Randolph
*Attorney, Agent, or Firm*—Neuman, Williams, Anderson & Olson

[57] ABSTRACT

Benzyl-substituted cyclooctanone compounds which exhibit hypocholesterolemic properties.

4 Claims, No Drawings

HYPOCHOLESTEROLEMIC COMPOUNDS

This application is a division of application Ser. No. 198,445 filed Nov. 12, 1971, now U.S. Pat. No. 3,781,444. Ser. No. 198,445 is a continuation-in-part of application Ser. No. 105,076 filed Jan. 8, 1971, now abandoned.

This invention relates to new compositions of matter having useful pharmacological properties.

Elevated levels of cholesterol in the blood stream are believed to play a significant role with respect to cardiovascular disease and particularly atherosclerosis. In the treatment and prevention of atherosclerosis it is desired to maintain normal blood cholesterol levels and/or to reduce blood cholesterol levels in hypercholesterolemic patients. It has now been found that chemical compounds having structural formulae I and II exhibit hypocholesterolemic properties:

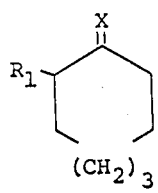 (Formula I)

where X = O, NOH, $NNH_2$, $NNHCH_3$, $NNHC_6Hhd 5$, $NN(CH_3)_2$ or $NNHCONH_2$, $R_1$ =

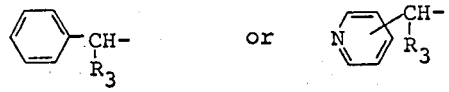

with $R_3$ being H, OH, $OCH_3$, $OC_2H_5$, $CH_3$ or $C_2H_5$ and the aromatic ring being unsubstituted or substituted with not more than three substituents selected from Cl, F, CN, $NH_2$, $CF_3$, OH, lower alkyl, lower alkoxy, lower alkylamino and lower dialkylamino, and

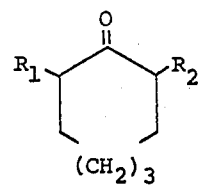 (Formula II)

where $R_1$ and $R_2$ =

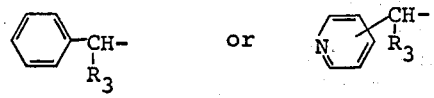

with $R_3$ being H, OH, $OCH_3$, $OC_2H_5$, $CH_3$ or $C_2H_5$ and the aromatic ring in each of $R_1$ and $R_2$ being independently unsubstituted or substituted with not more than three substituents selected from Cl, F, CN, $NH_2$, $CF_3$, OH, lower alkyl, lower alkoxy, lower alkylamino and lower dialkylamino.

The term "lower" as used herein in connection with alkyl or alkoxy groups refers to groups having from 1 to 5 carbon atoms.

Compositions which are particularly preferred in accordance with the present invention include compounds embraced by structural formulae III and IV:

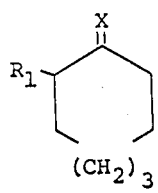 (Formula III)

where X = O, NOH, $NNH_2$, $NNHCH_3$, $NNHC_6H_5$, $NN(CH_3)_2$ or $NNHCONH_2$, $R_1$ =

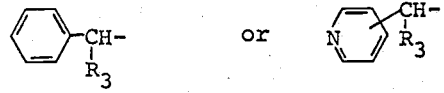

with $R_3$ being H, OH, $OCH_3$, $OC_2H_5$, $CH_3$ or $C_2H_5$ and the aromatic ring being unsubstituted or substituted with not more than three substituents selected from Cl, F, CN, $NH_2$, $CF_3$, OH, lower alkyl, lower alkoxy, lower alkylamino and lower dialkylamino provided that when X = O and the aromatic ring in $R_1$ is unsubstituted, $R_3$ is other than H or OH, and (Formula IV)

where $R_1$ and $R_2$ = with $R_3$ being H, OH, $OCH_3$, $OC_2H_5$, $CH_3$ or $C_2H_5$ and the aromatic ring in each of $R_1$ and $R_2$ being independently unsubstituted or substituted with not more than three substituents selected from Cl, F, CN, $NH_2$, $CF_3$, OH, lower alkyl, lower alkoxy, lower alkylamino and lower dialkylamino.

Preparation of the novel compounds of the invention is illustrated by the following examples.

EXAMPLE I

The 2-benzylcyclooctanones (Formula I) are prepared by low pressure hydrogenation of the corresponding 2-benzylidenecyclooctanones which, in turn, are obtained from cyclooctanone and the appropriately substituted benzaldehyde using the method of Braude et al. as described in *J. Chem. Soc.*, 4711–4719 (1957). The hydrogenation catalyst preferred is 5 percent palladium on carbon and ethanol is suitable as the solvent. Compounds prepared in this manner are 2-(p-chlorobenzyl)cyclooctanone, 2-(2,6-dichlorobenzyl)-cyclooctanone, 2-(m-fluorobenzyl)cyclooctanone, 2-(2-fluoro-6-chlorobenzyl)cyclooctanone, 2-(o-methylbenzyl)-cyclooctanone, 2-(m-trifluoromethylbenzyl)- cyclooctanone, 2-(p-methoxybenzyl)cyclooctanone, 2-(2,4-dimethoxybenzyl)cyclooctanone, 2-(2,4,5-trimethoxybenzyl)cyclooctanone, 2-(3,4-dihydroxybenzyl)cyclooctanone, 2-(2-hydroxy-3-methoxybenzyl)cyclooctanone, 2-(m-cyanobenzyl)cyclooctanone and 2-(2-chloro-4-dimethylaminobenzyl)cyclooctanone.

The oxime of 2-benzylcyclooctanone is prepared by placing an 18.5-gram portion of 2-benzylcyclooctanone as obtained above in 150 milliliters of a 1:1 mixture of ethanol and pyridine containing 15 grams of hydroxylamine hydrochloride. The resulting mixture is heated for 3 hours at reflux temperatures. Most of the solvent mixture is then removed under reduced pressure and the residual oil is washed with water before dissolving in ether and washing the ether solution with several additional portions of water. Removal of the ether yields a solid which upon recrystallization from methanol gives crystalline 2-benzylcyclooctanone oxime, melting point 117°–119° C. Also prepared in a similar manner are the oxime derivatives of 2-(o-chlorobenzyl)-cyclooctanone, 2-(p-fluorobenzyl)cyclooctanone, 2-(m-methylbenzyl)-cyclooctanone, 2-(2,3-dichlorobenzyl)cyclooctanone, 2-(o-trifluoromethylbenzyl)cyclooctanone, 2-(o-methoxybenzyl)cyclooctanone, 2-(2,3-dimethoxybenzyl)cyclooctanone, 2-(p-hydroxybenzyl)cyclooctanone, 2-(3-ethyl-4-hydroxy-5-isopropyl)cyclooctanone, 2-(2-hydroxy-5-methoxybenzyl)cyclooctanone and 2-(p-dimethylaminobenzyl)cyclooctanone.

The hydrazones, methylhydrazones, N,N-dimethylhydrazones, phenylhydrazones and semicarbazones of the 2-benzylcyclooctanones are prepared using the general procedures described by L. F. Fieser and M. Fieser in *Reagents for Organic Synthesis*, John Wiley and Sons, Inc., New York, N.Y., 1967, especially pages 290, 436, 838 and 1000. Compounds converted to the hydrazone, methylhydrazone, N,N-dimethylhydrazone, phenylhydrazone and semicarbazone derivatives using these procedures are 2-(m-chlorobenzyl(cyclooctanone, 2-(p-methylaminobenzyl)cyclooctanone, 2-(p-isopropylbenzyl)cyclooctanone, 2-(3,4-dichlorobenzyl)cyclooctanone, 2-(o-fluorobenzyl)-cyclooctanone, 2-(3,5-dichloro-4-hydroxybenzyl)cyclooctanone, 2-(p-methylbenzyl)cyclooctanone, 2-(p-trifluoromethylbenzyl)cyclooctanone, 2-(m-methoxybenzyl)cyclooctanone, 2-(2,5-dimethoxybenzyl)cyclooctanone, 2-(2,4,6-trimethoxybenzyl)cyclooctanone, 2-(o-hydroxybenzyl)cyclooctanone, 2-(2,5-dihydroxybenzyl)cyclooctanone, 2-(2-hydroxy-4,6-dimethoxybenzyl)cyclooctanone, 2-(p-cyanobenzyl)cyclooctanone and 2-(p-diethylaminobenzyl)cyclooctanone.

EXAMPLE II 2,8-Dibenzylcyclooctanone is prepared by stirring 25 grams of cyclooctanone, 54 grams of benzaldehyde, 30 grams of potassium hydroxide and 500 milliliters of methanol at reflux temperatures for 4 hours. The mixture is then cooled to room temperature and 200 milliliters of water are added followed by 300 milliliters of ether. The ether layer is separated and the ether and methanol are then removed by distillation. The residue is taken up in 200 milliliters of ethanol and hydrogenated at 1,000 p.s.i.g. and ambient temperature using a 10 percent palladium on carbon catalyst. The catalyst is removed by filtration and the solvent is removed by distillation. Recrystallization of the crude product is effected by dissolving in 150 milliliters of methanol and seeding with crystalline 2,8-dibenzylcyclooctanone (m.p. 75°–77° C.). Cooling of the seeded methanolic solution gives 16 grams of crystals with melting point 60°–67° C. A second recrystallization of this material from methanol gives one isomer of 2,8-dibenzylcyclooctanone, melting point 75°–77° C., as a first crop and a second isomer of 2,8-dibenzylcyclooctanone, melting point 66°–68° C., as a second crop.

EXAMPLE III

A mixture consisting of cyclooctanone (12.5 grams), benzaldehyde (27 grams), potassium hydroxide (30 grams) and 200 milliliters of methanol is stirred at reflux temperatures for 4 hours and is allowed to stand overnight. The crystalline precipitate which forms is collected by filtration and is washed with hot methanol to give 17 grams of 2-benzylidene-8-($\alpha$-methoxybenzyl)cyclooctanone, melting point 136°–139° C. Hydrogenation of a 10-gram portion of this material at 60 p.s.i.g. in 300 milliliters of ethanol using 10 percent palladium on carbon as the catalyst gives 3.9 grams of 2-benzyl-8-($\alpha$-methoxybenzyl)cyclooctanone, melting point 104°–106° C., as a first crop of crystals from ethanol. Removal of a second crop of crystals and concentration of the mother liquor yields 1.1 grams of an isomeric 2-benzyl-8-($\alpha$-methoxybenzyl)cyclooctanone, melting point 83°–84° C.

The above described procedure is also used in preparing 2-(p-chlorobenzyl)-8-(p-chloro-$\alpha$-methoxybenzyl)cyclooctanone, 2-(3,5-dichlorobenzyl)-8-(3,5-dichloro-$\alpha$-methoxybenzyl)cyclooctanone, 2-(p-fluorobenzyl)-8-(p-fluoro-$\alpha$-methoxybenzyl)cyclooctanone, 2-(2-fluoro-6-chlorobenzyl)-8-(2-fluoro-6-chloro-$\alpha$-methoxybenzyl)cyclooctanone, 2-(m-methylbenzyl)-8-(m-methyl-$\alpha$-methoxybenzyl)cyclooctanone, 2-(p-trifluoromethylbenzyl)-8-(p-trifluoromethyl-$\alpha$-methoxybenzyl)cyclooctanone, 2-(3,5-dimethoxybenzyl)-8-(3,5,$\alpha$-trimethoxybenzyl)cyclooctanone, 2-(3-methoxy-4-hydroxybenzyl)-8-(4-hydroxy-3,$\alpha$-dimethoxybenzyl)cyclooctanone, 2-(3,5-dimethoxy-4-hydroxybenzyl)-8-(4-hydroxy-3,5,$\alpha$-trimethoxybenzyl)cyclooctanone, 2-(p-cyanobenzyl)-8-(p-cyano-$\alpha$-methoxybenzyl)cyclooctanone and 2-(p-dimethylaminobenzyl)-8-(p-dimethylamino-$\alpha$-methoxybenzyl)cyclooctanone.

EXAMPLE IV

An alternative procedure for preparing 2,8-dibenzylcyclooctanones involves the corresponding 2,8-dibenzylidenecyclooctanones as the intermediates. Thus, a mixture comprising 12.5 grams of cyclooctanone, 27 grams of benzaldehyde, 15 grams of potassium hydroxide and 300 milliliters of methanol is stirred at reflux temperatures for 4 hours. To the hot, stirred mixture are slowly added 400 milliliters of t-butyl alcohol with simultaneous removal of the methanol by distillation. The mixture is then cooled, water is added and the product is extracted with ether. The crude product obtained from the ether extract is chromatographed on activated alumina to give 2,8-dibenzylidenecyclooctanone. This intermediate is hydrogenated at 60 p.s.i.g. in ethanol using 5 percent palladium on carbon. Fractional crystallization of the hydrogenation product from methanol affords the isomeric 2,8-dibenzylcyclooctanones, m.p. 75°–77° C. and 66°–68° C.

The foregoing procedure is also used for preparing 2,8-bis(p-chlorobenzyl)cyclooctanone, 2,8-bis(3,5-dichlorobenzyl)-cyclooctanone, 2,8-bis(o-fluorobenzyl)cyclooctanone, 2,8-bis(2-fluoro-6-chlorobenzyl)-cyclooctanone, 2,8-bis(o-methylbenzyl)cyclooctanone, 2,8-bis(m-trifluoromethylbenzyl)cyclooctanone, 2,8-bis(p-butylbenzyl)cyclooctanone, 2,8-bis(p-methoxybenzyl)cyclooctanone, 2,8-bis(3,4-dimethoxybenzyl)cyclooctanone, 2,8-bis-(3,4,5-trimethoxybenzyl)cyclooctanone, 2,8-bis(m-hydroxybenzyl)-cyclooctanone, 2,8-bis(3-hydroxy-4-methoxybenzyl)cyclooctanone and 2,8-bis(3,5-dimethyl-4-hydroxybenzyl)cyclooctanone.

EXAMPLE V 2,8-Disubstituted cyclooctanones which are unsymmetrically substituted are prepared from 2-benzylcyclooctanones which have been previously prepared by the procedure of Example I or by the procedure for 2-benzylcyclooctanone as described by R. P. Houghton and E. S. Waight in *J. Chem. Soc.*, 978–981 (1969). The particular 2-benzylcyclooctanone is placed in a methanolic solution of the desired aromatic aldehyde and potassium hydroxide and the resulting mixture is stirred at reflux temperatures for a period of time. The crude product is recovered by ether extraction and subjected to hydrogenation at 60 p.s.i.g. in ethanol using 5 percent palladium on carbon as the catalyst to give the unsymmetrical 2,8-disubstituted cyclooctanones.

Compounds prepared by the foregoing procedure are 2-(m-chlorobenzyl)-8-(3,5-dichlorobenzyl)cyclooctanone, 2-(o-fluorobenzyl)-8-(p-hydroxybenzyl)cyclooctanone, 2-benzyl-8-(2,4,6-trimethylbenzyl)cyclooctanone, 2-(3,4-dichlorobenzyl)-8-(3-ethoxy-4-hydroxybenzyl)cyclooctanone, 2-(p-methoxybenzyl)-8-(3,4,5-trimethoxybenzyl)cyclooctanone, 2-(p-dimethylaminobenzyl)-8-(3,5-dimethyl-4-hydroxybenzyl)-cyclooctanone, 2-benzyl-8-(2-fluoro-6-chlorobenzyl)-cyclooctanone, 2-(m-methylbenzyl)-8-(3-methoxy-4-hydroxybenzyl)cyclooctanone, 2-(p-cyanobenzyl)-8-(p-diethylaminobenzyl)cyclooctanone, 2-(o-hydroxybenzyl)-8-(p-trifluoromethylbenzyl)cyclooctanone, 2-benzyl-8-(p-chlorobenzyl)cyclooctanone and 2-benzyl-8-(4-pyridylmethyl)cyclooctanone.

EXAMPLE VI

2-Benzylidenecyclooctanones are prepared according to the procedure of Braude et al. as described in *J. Chem. Soc.*, 4711–4719 (1957). The 2-benzylidenecyclooctanones are then subjected to condensation reaction conditions (such as methanolic potassium hydroxide) in the presence of equimolar amounts of a desired benzaldehyde to give substituted-benzyl 2-benzylidene-8-(α-alkoxybenzyl)cyclooctanones. Hydrogenation of these intermediates at 60 p.s.i.g. in the presence of 5 percent palladium on carbon gives the corresponding 2-benzyl-8-(α-alkoxybenzyl)cyclooctanones wherein the substitution on the aromatic rings is different. Compounds prepared by this procedure are 2-benzyl-8-(p-chloro-α-methoxybenzyl)cyclooctanone, 2-(p-chlorobenzyl)-8-(α-methoxybenzyl)cyclooctanone, 2-(3,4-dichlorobenzyl)-8-(m-chloro-α-methoxybenzyl)cyclooctanone, 2-(2-fluoro-6-chlorobenzyl)-8-(o-fluoro-α-methoxybenzyl)cyclooctanone, 2-(p-methylbenzyl)-8-(α-methoxybenzyl)cyclooctanone, 2-(m-trifluoromethyl)-8-(p-methyl-α-methoxybenzyl)cyclooctanone, 2-(o-methoxybenzyl)-8-(p,α-dimethoxybenzyl)cyclooctanone, 2-(3,4-dimethoxybenzyl)-8-(p-hydroxy-α-methoxybenzyl)cyclooctanone, 2-(2,4-diethoxy-5-ethylbenzyl)-8-(m-ethyl-α-methoxybenzyl)cyclooctanone, 2-(2-hydroxy-3-methoxybenzyl)-8-(m-chloro-α-methoxybenzyl)cyclooctanone, 2-(3,5dimethoxy-4-hydroxybenzyl)-8-(3,4,5, α-tetramethoxybenzyl)cyclooctanone, 2(p-cyanobenzyl)-8-(m-fluoro-α-methoxybenzyl)cyclooctanone, 2-(p-diethylaminobenzyl)-8-(m-cyano-α-methoxybenzyl)-cyclooctanone, 2-(2-chloro-4-dimethylamino)-8-(p-chloro-α-methoxybenzyl)cyclooctanone and 2-(p-chlorobenzyl)-8-(2-chloro-4-dimethylamino-α-methoxybenzyl)cyclooctanone.

EXAMPLE VII

This example illustrates the preparation of benzylcyclooctanones wherein the aromatic ring is substituted with an amino group. 2-Benzylcyclooctanone is allowed to react with equimolar amounts of p-nitrobenzaldehyde in refluxing methanolic potassium hydroxide for 3 hours. The 2-benzyl-8-(p-nitrobenzylidene)cyclooctanone which forms is removed by filtration and subjected to hydrogenation at 50 p.s.i.g. in the presence of 10 percent palladium on carbon using a solvent system comprising equal portions of ethyl acetate and acetic acid. The 2-benzyl-8-(p-aminobenzyl)cyclooctanone which is obtained from the hydrogenation is purified by converting it to the hydrochloride salt by means of hydrogen chloride introduced into an ethereal solution of the crude product. The melting point of the crude 2-benzyl8-(p-aminobenzyl)cyclooctanone hydrochloride is 175°–195° C.

In a similar manner are prepared 2-(2,4-diaminobenzyl)-cyclooctanone, 2-(m-aminobenzyl)cyclooctanone, 2-(m-chlorobenzyl)-8-(p-aminobenzyl)cyclooctanone, 2-(m-aminobenzyl)-8-(3,4-dichlorobenzyl)cyclooctanone, 2-(o-fluorobenzyl)-8-(m-aminobenzyl)-cyclooctanone, 2-(p-aminobenzyl)-8-(m-trifluoromethylbenzyl)cyclooctanone, 2-(p-aminobenzyl)-8-(o-methoxybenzyl)cyclooctanone, 2-(p-aminobenzyl)-8-(3-hydroxy-4-methoxybenzyl)cyclooctanone and 2-(p-aminobenzyl)- 8-(p-dimethylaminobenzyl)cyclooctanone.

EXAMPLE VIII

The preparation of (α-hydroxybenzyl)cyclooctanones is effected using the general procedure of Braude et al. in *J. Chem. Soc.*, 4717 (1957) for making 2-(α-hydroxybenzyl)cyclooctanone. For the preparation of 2,8-disubstituted cyclooctanones such as 2-benzyl-8-(α-hydroxybenzyl)cyclooctanone, low pressure hydrogenation in the presence of palladium on carbon is effective in reducing the olefinic bond in 2-benzylidene-8-(α-hydroxybenzyl)cyclooctanone which has been previously reported by R. Cornubert et al. in *Bull. soc. chim.* 5, 1493 (1938). Using the basic procedures mentioned, the following compounds are prepared: 2-(3-fluoro-4-chloro-α-hydroxybenzyl)cyclooctanone, 2-(3-fluoro-4-ethoxy-α-hydroxybenzyl)cyclooctanone, 2-(p-dimethylamino-α-hydroxybenzyl)cyclooctanone, 2-(2,4-dichlorobenzyl)-8-(2,4-dichloro-α-hydroxybenzyl)cyclooctanone, 2-(p-trifluoromethylbenzyl)-8-(p-trifluoromethyl-α-hydroxybenzyl)cyclooctanone, 2-(p-isopropylbenzyl)-8-(p-isopropyl-α-hydroxybenzyl)cyclooctanone and 2-(3-pyridylmethyl)-8-(α-hydroxy-3-pyridylmethyl)cyclooctanone.

The hypocholesterolemic properties of the new compounds of the invention are shown by the following test data obtained by orally administering aqueous suspensions of the compounds to rats for a period of 5 days. The animals were fasted overnight prior to the fifth day of the experiment and the blood samples were obtained via cardiac puncture 2 hours after the last drug administration. The blood samples were then analyzed for total cholesterol.

TABLE I

| Compound | Dose (mg/kg of body weight) | % Reduction of Serum Cholesterol Level From Control Level |
|---|---|---|
| 2-Benzylcyclooctanone oxime | 200 | 23 |
| 2,8-Dibenzylcyclooctanone (m.p. 75–77° C.) | 100 | 71 |
| " | 50 | 68 |
| " | 25 | 63 |
| " | 12.5 | 68 |
| " | 6.25 | 54 |
| " | 3.13 | 40 |
| " | 1.57 | 41 |
| " | 0.79 | 8 |
| 2,8-Dibenzylcyclooctanone (m.p. 66–68° C.) | 10 | 51 |
| 2-Benzyl-8-(α-methoxybenzyl)cyclooctanone (m.p. 104–106° C.) | 100 | 22 |
| 2-Benzyl-8-(α-methoxybenzyl)cyclooctanone (m.p. 83–84° C.) | 100 | 66 |
| 2-benzyl-8-(4-pyridylmethyl)-cyclooctanone hydrochloride | 100 | 27 |

The ability of compounds of this invention to lower serum cholesterol levels in the rat is seen from the above data. In addition to the ability to lower serum cholesterol levels, hypocholesterolemic agents desirably should not produce an accumulation of cholesterol intermediates such as desmosterol which are in themselves atherogenic. In this connection, a particularly preferred compound of this invention was compared with [ethyl α-(p-chlorophenoxy)isobutyrate (CPIB)], a drug in current clinical use. This involved a comparison of the hepatic cholesterol synthesis in animals. The parameters of special interest were alterations in cholesterol synthesis as measured by in vitro incorporation of $C^{14}$-labelled mevalonic acid into various lipid classes (including cholesterol and cholesterol esters) in liver slices taken from drug-treated animals and by accumulation of desmosterol or other atherogenic sterol intermediates.

Three randomly selected groups of rats weighing approximately 150 grams each were fed ad libitum throughout the experiment. Animals were given daily doses of an aqueous suspension of the appropriate drug or water orally by hypodermic syringe.

Group A — Water only
Group B — CPIB, 200 mg/kg daily
Group C — 2,8-Dibenzylcyclooctanone (m.p. 75°–77° C.), 100 mg/kg daily At appropriate intervals over a period of 28 days, one rat from each group was sacrificed and liver slices were prepared in duplicate for incubation with mevalonic-2-$C^{14}$ acid. The degree of incorporation of mevalonic-2-$C^{14}$ acid into the various lipid classes present in the liver tissue was determined and the data indicated that there was no gross inhibition in the biosynthesis of either cholesterol or cholesterol esters in the Group B and Group C animals as compared with the control group. Moreover, there was no accumulation of sterol intermediates such as desmosterol apparent in the Group C animals relative to the control group.

The compounds of this invention can be used as hypocholesterolemic agents at relatively low dosage levels. In general, they can be employed in amounts ranging from about 1.0 to 500 mg/kg of the host body weight. As can be seen from the data in Table I, hypocholesterolemic activity is exhibited by each of the 2,8-dibenzylcyclooctanone isomers isolated as well as by each of the 2-benzyl-8-(α-methoxybenzyl)cyclooctanone isomers obtained. It is preferred that the compounds be administered orally, but it is apparent that other means of administration may be equally effective. When given orally, the compounds can be administered in tablet form or as aqueous suspensions or emulsions. Compounds which are capable of forming acid addition salts may be administered in that form provided, of course, that therapeutically acceptable salts are used. Thus, for example, aminobenzyl- and pyridylmethyl-substituted cyclooctanones may be converted to the corresponding hydrochloride, sulfate, phosphate, acetate, tartrate or gluconate salts and used in that form.

Those modifications and equivalents which fall within the spirit of the invention are to be considered a part thereof.

What is claimed is:

1. As new compositions of matter compounds of the formula

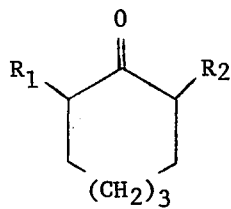

where $R_1$ and $R_2$ =

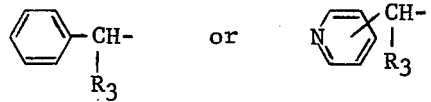

with $R_3$ being H, OH, $OCH_3$, $OC_2H_5$, $CH_3$ or $C_2H_5$ and the aromatic ring in each of $R_1$ and $R_2$ being independently unsubstituted or substituted with not more than three substituents selected from Cl, F, CN, $NH_2$, $CF_3$, OH, lower alkyl, lower alkoxy, lower alkylamine and lower dialkylamino.

2. 2,8-Dibenzylcyclooctanone.

3. 2-Benzyl-8-(α-methoxybenzyl)cyclooctanone.
4. 2-Benzyl-8-(4-pyridylmethyl)cyclooctanone hydrochloride.

* * * * *

UNITED STATES PATENT OFFICE
CERTIFICATE OF CORRECTION

PATENT NO. : 3,937,710
DATED : February 10, 1976
INVENTOR(S) : BOBBY E. EZZELL, EUGENE R. FLUCK and LOUIS R. HAEFELE It is certified that error appears in the above-identified patent and that said Letters Patent are hereby corrected as shown below:

Column 1, line 30, "NNHC$_6$Hhd 5" should be -- NNHC$_6$H$_5$ --

Column 3, line 28 "hydroxy-5-isopropyl)cyclooctanone" should be -- hydroxy-5-isopropylbenzyl)cyclooctanone --

Column 6, line 2, "2-(3,5dime-" should be -- 2-(3,5-dime- -- line 4, "2(" should be -- 2-( -- line 28, "2-benzyl8-(p-aminobenzyl)cyclooctanone" should be -- 2-benzyl-8-(p-aminobenzyl)cyclooctanone --

Signed and Sealed this fourth Day of May 1976

[SEAL]

Attest:

RUTH C. MASON
Attesting Officer

C. MARSHALL DANN
Commissioner of Patents and Trademarks